United States Patent
Hoffman et al.

(10) Patent No.: US 8,318,654 B2
(45) Date of Patent: Nov. 27, 2012

(54) CLEANSING COMPOSITION INCORPORATING A BIOCIDE, HEATING AGENT AND THERMOCHROMIC SUBSTANCE

(75) Inventors: Douglas Robert Hoffman, Greenville, WI (US); David William Koenig, Menasha, WI (US); Scott W. Wenzel, Neenah, WI (US); Philip E. Kieffer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/606,630

(22) Filed: Nov. 30, 2006

(65) Prior Publication Data

US 2008/0132438 A1   Jun. 5, 2008

(51) Int. Cl.
   *C11D 3/00* (2006.01)
   *C11D 17/00* (2006.01)
   *C11D 7/06* (2006.01)
   *C10L 10/06* (2006.01)

(52) U.S. Cl. ........ 510/380; 510/349; 510/441; 510/443; 510/186; 510/196

(58) Field of Classification Search .......... 510/349, 510/441, 443, 186, 196, 252, 297, 298
See application file for complete search history.

(56) References Cited

U.S. PATENT DOCUMENTS

| | | | |
|---|---|---|---|
| 3,341,418 A | 9/1967 | Moses et al. | |
| 3,585,982 A * | 6/1971 | Hollinshead | 126/263.1 |
| 3,600,060 A | 8/1971 | Churchill et al. | |
| 3,619,254 A | 11/1971 | Davis | |
| 3,702,302 A | 11/1972 | Wilson | |
| 3,722,752 A | 3/1973 | Kenkare et al. | |
| 4,022,706 A | 5/1977 | Davis | |
| 4,088,751 A * | 5/1978 | Kenkare et al. | 424/47 |
| 4,100,324 A | 7/1978 | Anderson et al. | |
| 4,110,426 A | 8/1978 | Barnhurst et al. | |
| 4,159,316 A | 6/1979 | Januszewski et al. | |
| 4,187,287 A | 2/1980 | Schreiber et al. | |
| 4,349,533 A | 9/1982 | Dent et al. | |

(Continued)

FOREIGN PATENT DOCUMENTS

EP   0897719   7/1996

(Continued)

OTHER PUBLICATIONS

Article—O'Brien-Simpson, NM et al. *An Immune Response Directed to Proteinase and Adhesin Functional Epitopes Protects against Prophyromonas Gingivalis-Induced Periodontal Bone Loss* J. Immunol., 175:3980-389 2005.

(Continued)

*Primary Examiner* — Ling Choi
*Assistant Examiner* — Thuy-Ai Nguyen
(74) *Attorney, Agent, or Firm* — Dority & Manning, P.A.

(57) ABSTRACT

A cleansing composition is described. The cleansing composition generally contains an antimicrobial agent, a heating agent, and a thermochromic agent. During use, the heating agent heats the composition so that the antimicrobial agent becomes more effective. The thermochromic agent, on the other hand, changes the color of the composition as it is heated in order to indicate to a user that the composition is at a desired temperature. In an alternative embodiment, instead of containing a heating agent, a heating source can be used to heat the composition. The heating source can be, for instance, an electrical resistance heater.

24 Claims, 2 Drawing Sheets

U.S. PATENT DOCUMENTS

| | | | |
|---|---|---|---|
| 4,362,715 A | 12/1982 | Strianse et al. | |
| 4,379,143 A | 4/1983 | Sherry et al. | |
| 4,439,416 A | 3/1984 | Cordon et al. | |
| 4,626,550 A | 12/1986 | Hertzenberg | |
| 4,839,081 A | 6/1989 | Church et al. | |
| 4,957,949 A | 9/1990 | Kamada et al. | |
| 5,091,102 A * | 2/1992 | Sheridan | 15/104.93 |
| 5,284,703 A | 2/1994 | Everhart et al. | |
| 5,350,624 A | 9/1994 | Georger et al. | |
| 5,431,697 A | 7/1995 | Kamata et al. | |
| 5,827,870 A * | 10/1998 | Chodosh | 514/390 |
| 6,180,584 B1 | 1/2001 | Sawan et al. | |
| 6,217,889 B1 | 4/2001 | Lorenzi et al. | |
| 6,228,389 B1 | 5/2001 | McCue et al. | |
| 6,232,282 B1 * | 5/2001 | Kvietok et al. | 510/357 |
| 6,267,975 B1 | 7/2001 | Smith, III et al. | |
| 6,270,783 B1 | 8/2001 | Slavtcheff et al. | |
| 6,287,584 B1 | 9/2001 | Feuer et al. | |
| 6,303,108 B1 | 10/2001 | Roulier et al. | |
| 6,309,655 B1 | 10/2001 | Minnix | |
| 6,322,801 B1 | 11/2001 | Lorenzi et al. | |
| 6,423,329 B1 * | 7/2002 | Sine et al. | 424/405 |
| 6,428,799 B1 | 8/2002 | Cen et al. | |
| 6,461,623 B2 | 10/2002 | Koike et al. | |
| 6,569,415 B1 * | 5/2003 | Orloff et al. | 424/73 |
| 6,726,386 B1 | 4/2004 | Gruenbacher et al. | |
| 6,733,766 B2 | 5/2004 | Gott et al. | |
| 6,752,998 B2 | 6/2004 | Verdrel-Lahaxe et al. | |
| 6,827,080 B2 | 12/2004 | Fish et al. | |
| 6,918,138 B2 | 7/2005 | Donovan | |
| 7,067,140 B2 | 6/2006 | Koike et al. | |
| 7,214,382 B2 | 5/2007 | Shefer et al. | |
| 7,250,174 B2 | 7/2007 | Lee et al. | |
| 7,268,104 B2 | 9/2007 | Krzysik et al. | |
| 2003/0008578 A1 * | 1/2003 | Brooks | 442/123 |
| 2003/0044366 A1 | 3/2003 | Dole et al. | |
| 2003/0056587 A1 * | 3/2003 | Carpenter et al. | 73/290 R |
| 2004/0063603 A1 * | 4/2004 | Dave et al. | 510/438 |
| 2004/0146475 A1 | 7/2004 | Peffly et al. | |
| 2005/0049157 A1 | 3/2005 | MacDonald et al. | |
| 2005/0107282 A1 | 5/2005 | Ford et al. | |
| 2005/0123573 A1 | 6/2005 | Spadini et al. | |
| 2005/0136098 A1 | 6/2005 | Spadini et al. | |
| 2005/0136238 A1 | 6/2005 | Lindsay et al. | |
| 2005/0136765 A1 | 6/2005 | Shannon | |
| 2005/0143278 A1 * | 6/2005 | Pegelow et al. | 510/439 |
| 2005/0187132 A1 * | 8/2005 | Blank et al. | 510/446 |
| 2005/0244211 A1 | 11/2005 | Brunner et al. | |
| 2006/0000043 A1 | 1/2006 | Jou-Chen et al. | |
| 2006/0002880 A1 | 1/2006 | Peffly et al. | |
| 2006/0003649 A1 | 1/2006 | Runge et al. | |
| 2006/0039886 A1 | 2/2006 | Shefer et al. | |
| 2006/0057084 A1 * | 3/2006 | Gonzalez | |
| 2006/0058206 A1 * | 3/2006 | Walls et al. | 510/130 |
| 2007/0142263 A1 | 6/2007 | Stahl et al. | |
| 2007/0145326 A1 | 6/2007 | Joseph et al. | |
| 2007/0145617 A1 | 6/2007 | Finney et al. | |
| 2007/0145618 A1 | 6/2007 | Finney et al. | |
| 2007/0148433 A1 | 6/2007 | Mallory et al. | |
| 2007/0148446 A1 | 6/2007 | Brown et al. | |
| 2007/0148447 A1 | 6/2007 | Amundson et al. | |
| 2007/0148448 A1 | 6/2007 | Joseph et al. | |
| 2007/0148459 A1 | 6/2007 | Joseph et al. | |
| 2007/0149435 A1 | 6/2007 | Koenig et al. | |

FOREIGN PATENT DOCUMENTS

| | | | |
|---|---|---|---|
| EP | 1393715 A1 | | 3/2004 |
| EP | 1634568 | | 7/2005 |
| JP | 63139083 | * | 6/1988 |
| JP | 06080534 | | 9/1992 |
| JP | 08059455 | | 8/1994 |
| WO | WO 9308793 | | 5/1993 |
| WO | WO 0112149 | | 2/2001 |
| WO | WO 0112150 | | 2/2001 |
| WO | WO 2005087043 | | 9/2005 |
| WO | WO 2005093029 | | 10/2005 |
| WO | WO 2005123023 | | 12/2005 |
| WO | WO 2006137955 | | 12/2006 |
| WO | WO 2007070118 | | 6/2007 |
| WO | WO 2007078460 | | 7/2007 |

OTHER PUBLICATIONS

Article—Heilmann, C. et al. *The multifunctional Staphlyococcus aureus Autolysin aaa Mediates Adherence to Immobolized Fibrinogen and Fibronectin* Immun. 73:4793-4802 2005.

Article—Dorsey, CW et al. *Samonella Enterica Serotype Typhimimurium MisL is an Intenstinal Colonization Factor that Binds Fibronectin* Mol. Microbiol., 57:196-211 2005.

Article—Pracht, D. et al. *PavA of Streptococcus pneumonaie Modulates Adherence, Invasion, and Meningeal Inflammation* Infect. Immun., 73:2680-2689 2005.

Article—Alberti-Segui, C. et al. *Identification of Potential Cell-Surface Proteins in Candida albicans and Investigation of the Role of a Putative-Cell Surface Glycosidase in Adhesion and Virulence* Yeast, 21:285-302 2004.

Article—Creti, R. et al. *Survey for Virulence Determinants among Enterococcus faecalis Isolated from Different Sources* J. Med. Microbiol., 53:12-20 2004.

Article—Coburn, J. and Cugini, *Targeted Mutation of the Outer Membrane Protein P66 Disrupts Attachment of the Lyme Disease Agent, Borrelia burgdorferi, to Integrin Alphavbeta3* Proc. Natl. Acad. Sci. USA, 100:7301-7306 2003.

Article—Carnoy, C. et al. *Pseudomonas aeruginosa Outer Membrance Adhesions for Human Respiratory Mucus Glycoproteins* Infect. Immun. 62:1896-1900 1994.

Article—Burch, PT et al. *Mortality in Murine Peritonitis Correlates with Increased Escherichia coli Adherence to the Intestinal Mucosa* Am. Surg. 70:333-341 2004.

Article—Mitchell, E. et al *Structural Basis for Oligosaccharide-Mediated Adhesion of Pseudomonas aeruginosa in the Lungs of Cystic Fibrosis Patients* Nat. Struct. Biol., 2002 9:918-921 2002.

Article—Silva de Souza, SM, et al. *Influence of Stannous Chloride on the Adhesive Properties of Corynebacterium diphtheriae Strains* Int. J. Mol. Med. 12:657-651 2003.

Article—Redford P. et al. *DegS is Necessary for Virulence and is Among Extraintestinal Escherichia coli Genes Induced in Murine Peritonitis* Infect. Immun. 71:3088-3096 2003.

Article—Isberg, RR and Barnes, P *Dancing with the Host; Flow-Dependent Bacterial Adhesion* Cell. 110:1-4 2002.

Article—Thomas, EW et al. *Bacterial Adhesion to Target Cells Enhanced by Shear Force* Cell. 109-913-923 2002.

Article—Knobloch, JKM et al. *Biofilm Formation by Staphylococcus epidermidis Depends on Functional RsbU, an Activator of the sigB Operon; Differential Activation Mechanisms due to Ethanol and Salt Stress* J. Bacteriol., 183:2624-2633 2001.

Article—Rachid, S. et al. *Effect of Subinhibitory Antibiotic Concentrations on Polysaccharide Intercellular Adhesion Expression in Biofilm-Forming Staphylococcus epidermidis* Antimicrob. Agents Chemother. 44:3357-3363 2000.

Article—Knobloch, JKM et al. *Alcoholic Ingredients in Skin Disinfectants Increase Biofilm Expression of Staphylococcus epidermidis* J. Antimicrob. Chemother. 49:683-687 2002.

Article—Gravesen A. et al. *Surface Attachment of Listeria monocytogenes is Induced by Sublethal Concentrations of Alcohol at Low Temperatures* Appl. Environ. Microbiol. 71:5601-5603 2005.

Article—Heiniger N. et al. *Influence of Temperature and Growth Phase on Expression of the Adhesion UspA1 by Moraxella catarrhalis* In re: American Society for Microbiology 105th General Meeting Abstracts B-228 2005.

PCT Search Report dated Feb. 5, 2008 for International Application No. PCT/IB2007/054231 filed Oct. 17, 2007.

US 6,290,977, 09/2001, Friars et al. (withdrawn)

* cited by examiner

CLEANSING COMPOSITION INCORPORATING A BIOCIDE, HEATING AGENT AND THERMOCHROMIC SUBSTANCE

BACKGROUND

One of the most effective methods found to date for limiting the spread of communicable disease is through effective cleansing of both animate and inanimate surfaces. Consumers have used liquid soap, spray cleaners, wet wipes, and related products for some time to remove disease-causing microbes from surfaces.

Recent research has suggested that specific environmental factors can impact microbial surface attachment, either increasing or decreasing the amount of microbes that adhere to a surface during cleaning. For example, sub-lethal concentrations of alcohol have been reported to increase the attachment and biofilm expression of *S. epidermidis* and *L. monocytogenes* on surfaces. More particularly, attachment of *L. monocytogenes* has been found to increase further when sub-lethal alcohol levels were coupled with exposure to low temperatures.

A cleansing composition, such as those currently available to consumers, may remove a proportionate amount of the microbes present on an adjacent surface when used as a disinfectant. However, based on the above mentioned research, the microorganisms remaining after cleansing with the composition may have increased microbial surface attachment and biofilm expression.

As such, a need currently exists for a cleansing product that improves upon the disinfecting properties of currently available commercial products. Furthermore, a need exists for visual evidence that the desired cleaning efficacy has been achieved. For example, a need exists for a hand soap comprising a biocide that heats to a temperature to effectively disinfect while also indicating the point at which proper sanitation has been achieved.

SUMMARY

In general, the present disclosure is directed to an improved cleansing composition. The cleansing composition, for instance, may comprise a body wash, a facial soap, a shampoo, a baby wash, a pet detergent or wash, a disinfectant, a general purpose cleaner, a window cleaner, a detergent, a vehicle cleaner, or any other suitable cleaning product. In one particular embodiment, the cleansing composition may comprise a hand soap composition. In accordance with the present disclosure, the cleansing composition contains an antimicrobial agent, a heating agent, and a thermochromic agent. Specifically, the heating agent is configured to activate during use of the cleansing composition causing an increase in temperature. The thermochromic agent is configured to cause a change in color of the cleansing composition in response to the increase in temperature. In accordance with the present disclosure, once the cleansing composition reaches a selected temperature, the composition can be configured to discontinue changing color indicating to the user that the desired temperature for microbe removal has been reached.

The cleansing composition of the present disclosure comprises an antimicrobial agent such as an isothiazolone, alkyl dimethyl ammonium chloride, a triazine, 2-thiocyanomethylthio benzothiazol, methylene bis thiocyanate, acrolein, dodecylguanidine hydrochloride, a chlorophenol, a quaternary ammonium salt, gluteraldehyde, a dithiocarbamate, 2-mercatobenzothiazole, para-chloro-meta-xylenol, silver, chlorohexidine, polyhexamthylene biguanide, a n-halamine, triclosan, a phospholipid, an alpha hydroxyl acid, 2,2-dibromo-3-nitrilopropionamide, 2-bromo-2-nitro-1,3-propanediol, farnesol, iodine, bromine, hydrogen peroxide, chlorine dioxide, ozone, a botanical oil, a botanical extract, benzalkonium chloride, chlorine, sodium hypochlorite, or combinations thereof.

In one embodiment, the antimicrobial of the present disclosure comprises an alcohol, for example, ethanol. In accordance with the present disclosure an alcohol may be present in the cleansing composition in an amount of at least about 30% by weight.

Another ingredient of the cleansing composition in accordance with the present disclosure is a heating agent. In one embodiment of the present disclosure, the heating agent comprises an electrolyte salt, which undergoes an exothermic reaction when contacted with water. More specifically, the electrolyte salt may comprise magnesium chloride, calcium chloride, aluminum chloride, calcium sulfate, sodium acetate, magnesium sulfate, sodium carbonate, sodium sulfate, or combinations thereof.

Other suitable heating agents may comprise a zeolite, a metal, slaked lime, quick lime, a glycol, polyvinyl amine, polyalkyleneamine, polyalkyleneimine, a metal oxide or combinations thereof.

The heating agent of the present disclosure may be encapsulated in a material that degrades during use of the cleansing composition. In one embodiment, the heating agent is encapsulated in a wax.

In one embodiment, a heating agent may be present in the cleansing composition in an amount of at least 5% by weight. In accordance with the present disclosure, the heating agent of the cleansing composition may be present, for instance, in an amount sufficient to cause the cleansing composition to increase in temperature from 20° C. to 25° C. when activated, such as from 20° C. to 30° C. when activated. In still another embodiment, the heating agent may be present in the cleansing composition in an amount sufficient to increase the temperature from 20° C. to 40° C. when activated. Depending on the surface to be cleansed, the initial and final temperatures of the cleansing composition may vary. For example, an adjacent surface such as a countertop may have a much lower initial temperature than a human hand. Also, depending on the amount and nature of the heating agent added, the final temperature of the cleansing composition can vary.

In accordance with the present disclosure, the cleansing composition may comprise a thermochromic agent designed to change color in response to the temperature increase of the cleansing composition. In one embodiment, the thermochromic agent comprises a leuco dye. The thermochromic agents of the present disclosure may change from one color to another, from a color to clear, or any other applicable color change.

Also, the thermochromic agent can be configured to change color at a specific temperature. In one embodiment, the thermochromic agent may change color at 25° C., in another instance at 30° C. Multiple thermochromic agents may be incorporated into the cleansing composition in order to create a gradual change in color of the cleansing composition that reflects the gradual change in temperature of the cleansing composition.

Additionally, the cleansing composition of the present disclosure may comprise a surfactant, an emollient, heat sink particles, a pH adjuster, a fragrance, any other suitable ingredients, or combinations thereof.

In accordance with the present disclosure, the cleansing system may comprise a cleansing composition comprising an antimicrobial agent and a thermochromic agent that is to be used in conjunction with a heating source. The heating source may comprise a microwave heater, an electrical resistance heater, an infrared heater, or any other suitable heating source. In the previous embodiment the cleansing composition can be contained in a dispensing device, and the heating source can heat the dispensing device, thereby heating the cleansing composition. In response to the temperature increase of the cleansing composition, the thermochromic agent may be activated causing a change in color of the cleansing composition. The color change may then signal to the user that the cleansing composition has reached an appropriate temperature for microbe removal.

The cleansing composition as described in the present disclosure may be in either liquid or solid form. Additionally, a wiper product comprising a substrate can contain the cleansing composition of the present disclosure. In one embodiment the substrate containing the cleansing composition comprises a nonwoven web.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
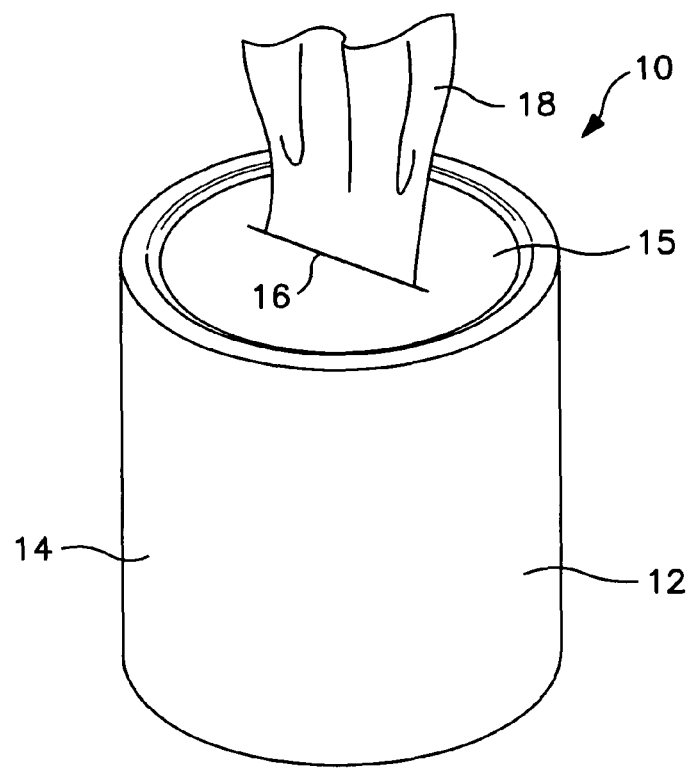
FIG. 1 is a perspective view of one embodiment of a cleansing composition as contained in a wiper product in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

The prevention of sickness and disease is extremely important to consumers, as evidenced by the numerous cleansing products currently commercially available for both personal cleansing and surface cleansing. However, recent research has indicated that while some cleansing compositions remove or kill a proportionate amount of microbes, those microbes remaining have increased surface attachment and biofilm expression. When a cleansing composition is used under low temperatures, microbial attachment increases further.

Therefore, if a cleansing composition is used at a low temperature, the composition intended to clean a surface may be causing microorganisms to attach to the surface. Additionally, if a cleansing composition does not have sufficient time to heat to the desired microbe-removing temperature, then the cleansing composition may not perform effectively.

The present disclosure, in one embodiment, is generally directed to a cleansing composition that is intended to increase in temperature and change color upon use. During use of the cleansing composition, a heating agent is activated which raises the temperature of the composition to a temperature which facilitates the removal of microbes from the skin. Also, the composition is intended to change color during use in order to indicate to a user when the desirable temperature has been reached, and, thus, sufficient microbe removal has occurred.

Another embodiment of the present disclosure is a cleansing composition that is heated by an outside heating source. The heating source comprises a microwave heater, an electrical resistance heater, or an infrared heater. A visual indicator is included in the cleansing composition to signal to the user when the cleansing composition has reached the desired temperature.

It should be understood that a variety of cleansing compositions may be made in accordance with the present disclosure. For instance, cleansing compositions that may be made in accordance with the present disclosure include hand soaps, shampoos, facial soaps, body washes, baby washes, and pet detergents or washes. Further, other cleansing compositions can also be formulated that may not be intended to wash part of a person's body. For instance, other cleansing compositions that may be made in accordance with the present disclosure include disinfectants, general purpose cleaners, window cleaners, detergents, vehicle cleaners, or any other suitable cleaning product. Furthermore, any of the cleansing compositions of the present disclosure, both for use on animate and inanimate objects, may be incorporated into nonwoven products, such as wet wipes, alcohol-based pads, moist clothes, or surface cleaning products.

The cleansing compositions of the present disclosure provide many benefits over the products that are currently commercially available. Foremost, the heating agent present in the cleansing composition of one embodiment allows for improved cleaning efficacy in comparison to other cleansing products. Additionally, the color change that occurs during use of the cleansing composition indicates to a user when the composition has reached the desired temperature for increased microbe removal. Therefore, the user does not have to rely on personal judgment as to whether or not the cleansing composition has reached a temperature sufficient for sanitation. The cleansing composition of the present disclosure increases in temperature and changes color, effectively removing microbes from cleansing surfaces and indicating when acceptable sanitation has been achieved. Thus, the cleansing composition as disclosed herein is an improvement on those products currently commercially available.

Generally, the cleansing compositions of the present disclosure are capable of killing or substantially inhibiting the growth of microbes. Specifically, the antimicrobial agent of the cleansing compositions interfaces with the metabolic pathways of the microbes to kill or inhibit the growth of the microbes.

Suitable antimicrobial agents for use in the cleansing compositions include, for example, isothiazolones, alkyl dimethyl ammonium chloride, triazines, 2-thiocyanomethylthio benzothiazol, methylene bis thiocyanate, acrolein, dodecylguanidine hydrochloride, chlorophenols, quarternary ammonium salts, gluteraldehyde, dithiocarbamates, 2-mercaptobenzothiazole, para-chloro-meta-xylenol, silver, chlorohexidine, polyhexamethylene biguanide, n-halamines, triclosan, phospholipids, alpha hydroxyl acids, 2,2-dibromo-3-nitrilopropionamide, 2-bromo-2-nitro-1,3-propanediol, farnesol, iodine, bromine, hydrogen peroxide, chlorine dioxide, alcohols, ozone, botanical oils (e.g., tee tree oil and rosemary oil), botanical extracts, benzalkonium chloride, chlorine, sodium hypochlorite, and combinations thereof.

In one embodiment of the present disclosure, the antimicrobial agent is alcohol. For instance, any suitable alcohol having antimicrobial properties may be used. In one embodiment, the alcohol may comprise ethyl alcohol or ethanol.

Alternatively, the alcohol may comprise isopropyl alcohol. In still another embodiment, a mixture of alcohols may be used.

The amount of antimicrobial agent present in the cleansing composition of the present disclosure depends on a variety of different factors. In one embodiment, especially when the composition contains an alcohol, the antimicrobial agents may be present in the cleansing composition in an amount of from about 30% by weight to about 90% by weight. Suitably, the antimicrobial agents are present in the cleansing composition in an amount of from 30% to 90% by weight, even more suitably from 40% to 80% by weight, and even more suitably from 50% to 70% by weight.

In accordance with the present disclosure, either a heating agent or a heat source is used to heat the cleansing composition.

In one embodiment, a heating agent is present in the cleansing composition. The heating agent releases heat during use of the cleansing composition and may result in a warm feeling on the skin or surface to be cleansed. Suitable heating agents for use in the cleansing composition include compounds which undergo an exothermic reaction, which begins during use of the cleansing composition. The heating agent of the present disclosure may comprise a zeolite, a metal, slaked lime, quick lime, a glycol, polyvinyl amine, polyalkyleneamine, polyalkyleneimine, a metal oxide, an electrolyte salt, or combinations thereof. Suitable electrolyte salts for use in the cleansing composition include, for example, calcium chloride, magnesium chloride, aluminum chloride, calcium sulfate, magnesium sulfate, sodium carbonate, sodium sulfate, sodium acetate or combinations thereof. The heating agent may be in either hydrous or anhydrous form.

The heating agent is generally included in the cleansing composition in amount of about 5% to about 40% by weight, more desirably from 5% to 30% by weight, and more desirably from 10% to 25% by weight.

In one embodiment of the present disclosure, the heating agent included in the cleansing composition is partially or completely surrounded by an encapsulation material prior to being introduced into the cleansing composition. The encapsulation material may degrade as a result of exposure to friction or an aqueous environment.

In one embodiment, the coating material used to coat the heating agent may comprise a hydrophobic wax material. As used herein, the term "hydrophobic wax material" means a material suitable to coat and protect the heating agent with temporary water protection during the timeframe of exposure to the aqueous environment; that is, the hydrophobic wax material may keep water from contacting the heating agent. Although the hydrophobic wax material provides protection of the heating agent, in one embodiment it will gradually dissolve away and off of the heating agent over time; that is, the hydrophobic wax material dissolves into the bulk of the cleansing composition over time and off of the heating agent so that the heating agent can be directly contacted with water upon activation in a wipe or other product.

In an alternative embodiment, the hydrophobic wax material does not substantially dissolve into the cleansing composition and off of the heating agent but is removed from the heating agent at the time of use through shearing or disruption of the hydrophobic wax material; that is, the hydrophobic wax material is mechanically broken off of the heating agent to allow the heating agent to access to water.

It may be desirable to have complete or partial coverage of the heating agent with the hydrophobic wax material to ensure that the heating agent is not susceptible to contact with water during the introduction of the cleansing composition into the aqueous liquid as described herein. When contacted with a substantially continuous layer of hydrophobic wax material, the heating agent can be encapsulated in a liquid environment without losing potency. Generally, the hydrophobic wax material may be applied to the heating agent in from about 1 to about 30 layers, desirably in from about 1 to about 10 layers.

Generally, the encapsulation material is present on the heating agent in an amount of from about 1% (by weight heating agent) to about 50% (by weight heating agent), desirably from about 1% (by weight heating agent) to about 40% (by weight heating agent), more desirably from about 1% (by weight heating agent) to about 30% (by weight heating agent), and even more desirably from about 1% (by weight heating agent) to about 20% (by weight heating agent). At these levels, there is sufficient hydrophobic wax material present on the heating agent to provide the desired level of protection, yet not too much to keep it from dissolving to allow for water to access the heating agent at the desired time.

Suitable hydrophobic wax materials for coating the heating agent are relatively low temperature melting wax materials. In one embodiment, the hydrophobic wax material has a melting temperature of less than about 140° C., desirably less than about 90° C. to facilitate the coating of the heating agent as described below.

Suitable hydrophobic wax materials for use in coating the heating agent (or other active agent) include, for example, organic ester and waxy compounds derived from animal, vegetable, and mineral sources including modifications of such compounds in addition to synthetically produced materials having similar properties. Specific examples that may be used alone or in combination include glyceryl tristearate, glyceryl distearate, canola wax, hydrogenated cottonseed oil, hydrogenated soybean oil, castor wax, rapeseed wax, beeswax, carnauba wax, candelilla wax, microwax, polyethylene, polypropylene, epoxies, long chain alcohols, long chain esters, long chain fatty acids such as stearic acid and behenic acid, hydrogenated plant and animal oils such as fish oil, tallow oil, and soy oil, microcrystalline waxes, metal stearates and metal fatty acids. Specific commercially available hydrophobic wax materials include, for example, Dynasan™ 110, 114, 116, and 118 (commercially available from DynaScan Technology Inc., Irvine, Calif.), Sterotex™ (commercially available from ABITEC Corp., Janesville, Wis.); Dritex C (commercially available from Dritex International, LTD., Essex, U.K.); Special Fat™ 42, 44, and 168T.

In accordance with the present disclosure, the cleansing composition may also contain at least one thermochromic agent that causes the cleansing composition to change color as the composition is heated during use. In general, any suitable thermochromic agent may be used in accordance with the present disclosure. Thermochromic agents are temperature sensitive agents that temporarily or permanently change color when exposed to heat.

Thermochromic agents come in various forms. For instance, in one embodiment, the thermochromic agent may comprise a leuco dye. In an alternative embodiment, the thermochromic agent may comprise liquid crystals. Most thermochromic agents undergo a color change from a specific color to colorless (i.e. clear) once heated to a certain temperature.

In accordance with the present disclosure, the cleansing composition contains at least one thermochromic agent so that the cleansing composition changes color after a long enough period of time to ensure proper washing, scrubbing or wiping. In one embodiment the cleansing composition comprises a single thermochromic agent; however, for some applications it may be beneficial for the cleansing composition to contain more than one thermochromic agent.

By incorporating a plurality of thermochromic agents into the cleansing composition, the composition can change color quickly after use and can continue to change color at successive temperatures for an overall period of time sufficient to indicate to the user that washing, scrubbing, or wiping is complete. For example, in one embodiment, the cleansing composition contains at least two thermochromic agents, and, in other embodiments, at least three or four thermochromic agents.

In general, the thermochromic agents may be present in the cleansing composition in an amount from about 0.1% to about 3% by weight, such as in an amount of about 1% by weight.

Any thermochromic substance that undergoes a color change at the desired temperature may generally be employed in the present disclosure. For example, liquid crystals may be employed as a thermochromic substance in some embodiments. The wavelength of light ("color") reflected by liquid crystals depends in part on the pitch of the helical structure of the liquid crystal molecules. Because the length of this pitch varies with temperature, the color of the liquid crystals is also a function of temperature. One particular type of liquid crystal that may be used in the present disclosure is a liquid crystal cholesterol derivative. Exemplary liquid crystal cholesterol derivatives may include alkanoic and aralkanoic acid esters of cholesterol, alkyl esters of cholesterol carbonate, cholesterol chloride, cholesterol bromide, cholesterol acetate, cholesterol oleate, cholesterol caprylate, cholesterol oleyl-carbonate, and so forth. Other suitable liquid crystal cholesterol derivatives are described in U.S. Pat. No. 3,600,060 to Churchill, et al.; U.S. Pat. No. 3,619,254 to Davis; and U.S. Pat. No. 4,022,706 to Davis, which are incorporated herein in their entirety by reference thereto for all purposes.

In addition to liquid crystals, another suitable thermochromic substance that may be employed in the present disclosure is a composition that includes a proton accepting chromogen ("Lewis base") and a solvent. The melting point of the solvent controls the temperature at which the chromogen will change color. More specifically, at a temperature below the melting point of the solvent, the chromogen generally possesses a first color (e.g., red). When the solvent is heated to its melting temperature, the chromogen may become protonated or deprotonated, thereby resulting in a shift of the absorption maxima. The nature of the color change depends on a variety of factors, including the type of proton-accepting chromogen utilized and the presence of any additional temperature-insensitive chromogens. Regardless, the color change is typically reversible.

Although not required, the proton-accepting chromogen is typically an organic dye, such as a leuco dye. In solution, the protonated form of the leuco dye predominates at acidic pH levels (e.g., pH of about 4 or less). When the solution is made more alkaline through deprotonation, however, a color change occurs. Of course, the position of this equilibrium may be shifted with temperature when other components are present. Suitable leuco dyes for use in the present disclosure may include, for instance, phthalides; phthalanes; substituted phthalides or phthalanes, such as triphenylmethan phthalides, triphenylmethanes, or diphenylmethanes; acyl-leucomethylene blue compounds; fluoranes; indolylphthalides; spiropyranes; cumarins; and so forth. Exemplary fluoranes include, for instance, 3,3'-dimethoxyfluorane, 3,6-dimethoxyfluorane, 3,6-dibutoxyfluorane, 3-chloro-6-phenylamino-fluorane, 3-diethylamino-6-dimethylfluorane, 3-diethylamino-6-methyl-7-chlorofluorane, and 3-diethyl-7,8-benzofluorane, 3,3'-bis-(p-dimethyl-aminophenyl)-7-phenylaminocluorane, 3-diethylamino-6-methyl-7-phenylamino-fluorane, 3-diethylamino-7-phenylaminofluorane, and 2-anilino-3-methyl-6-diethylamino-fluorane. Likewise, exemplary phthalides include 3,3',3"-tris(p-dimethylamino-phenyl)phthalide, 3,3'-bis(p-dimethyl-aminophenyl)phthalide, 3,3-bis(p-diethylamino-phenyl)-6-dimethylamino-phthalide, 3,(4-diethylaminophenyl)-3-(1-ethyl-2-methylindol-3-yl)phthalide, and 3-(4-diethylamino-2-methyl)phenyl-3-(1,2-dimethylindol-3-yl)phthalide.

Although any solvent for the thermochromic agent may generally be employed in the present disclosure, it is typically desired that the solvent have a low volatility. For example, the solvent may have a boiling point of about 150° C. or higher, and in some embodiments, from about 170° C. to 280° C. Likewise, the melting temperature of the solvent is also typically from about 25° C. to about 40° C., and in some embodiments, from about 30° C. to about 37° C. In one embodiment of the present disclosure, the cleansing composition comprises an alcohol that serves as both the antimicrobial agent and the solvent. Suitable solvents may include saturated or unsaturated alcohols containing about 6 to 30 carbon atoms, such as octyl alcohol, dodecyl alcohol, lauryl alcohol, cetyl alcohol, myristyl alcohol, stearyl alcohol, behenyl alcohol, geraniol, etc.; esters of saturated or unsaturated alcohols containing about 6 to 30 carbon atoms, such as butyl stearate, methyl stearate, lauryl laurate, lauryl stearate, stearyl laurate, methyl myristate, decyl myristate, lauryl myristate, butyl stearate, lauryl palmitate, decyl palmitate, palmitic acid glyceride, etc.; azomethines, such as benzylideneaniline, benzylidenelaurylamide, o-methoxybenzylidene laurylamine, benzylidene p-toluidine, p-cumylbenzylidene, etc.; amides, such as acetamide, stearamide, etc.; and so forth.

The thermochromic composition may also include a proton-donating agent (also referred to as a "color developer") to facilitate the reversibility of the color change. Such proton-donating agents may include, for instance, phenols, azoles, organic acids, esters or organic acids, and salts of organic acids. Exemplary phenols may include phenylphenol, bisphenol A, cresol, resorcinol, chlorolucinol, b-naphthol, 1,5-dihydroxynapthalene, pyrocatechol, pyrogallol, trimer of p-chlorophenol-formaldeyde condensate, etc. Exemplary azoles may include benzotriaoles, such as 5-chlorobenzotriazole, 4-laurylaminosulfobenzotriazole, 5-butylbenzotriazole, 2-oxybenzotriazole, 5-ethoxycarbonylbenzotriazole, 2-oxybenzotrizole, 5-ethoxycarbonylbenzotriazole, etc.; imidazoles, such as oxybenzimidazole, etc.; tetrazoles, and so forth. Exemplary organic acids may include aromatic carboxylic acids, such as salicylic acid, methylenebissalicylic acid, resorcylic acid, gallic acid, benzoic acid, p-oxybenzoic acid, pyromellitic acid, b-naphthoic acid, tannic acid, toluic acid, trimellitic acid, phthalic acid, terephthalic acid, anthranilic acid, etc.; aliphatic carboxylic acids, such as stearic acid, 1,2-hydroxystearic acid, tartaric acid, citric acid, oxalic acid, lauric acid, etc.; and so forth. Exemplary esters may include alkyl esters of aromatic carboxylic acids in which the alkyl moiety has 1 to 6 carbon atoms, such as butyl gallate, ethyl p-hydroxybenzoate, methyl salicylate, etc.

The amount of the proton-accepting chromogen employed may generally vary, but is typically from about 2% to about 20% by weight, and in some embodiments, from about 5% to about 15% bye weight of the thermochromic substance. Likewise, the proton-donating agent may constitute from about 5% to about 40% by weight, and in some embodiments, from about 10% to about 30% bye weight of the thermochromic substance. In addition, the solvent may constitute from about 50% to about 90% by weight, and in some embodiments, from about 65% to about 85% by weight of the thermochromic composition.

Regardless of the particular thermochromic substance employed, it may be microencapsulated to enhance the stability of the substance during processing. For example, the thermochromic substance may be mixed with a thermosetting resin according to any conventional method, such as interfacial polymerization, in-situ polymerization, etc. The thermosetting resin may include, for example, polyester resins, polyurethane resins, melamine resins, epoxy resins, diallyl phthalate resins, vinylester resins, and so forth. The resulting mixture may then be granulated and optionally coated with a hydrophilic macromolecular compound, such as alginic acid and salts thereof, carrageenan, pectin, gelatin, and the like, semisynthetic macromolecular compounds such as methylcellulose, cationized starch, carboxymethylcellulose, carboxymethylated starch, vinyl polymers (e.g., polyvinyl alcohol), polyvinylpyrrolidone, polyacrylic acid, polyacrylamide, maleic acid copolymers, and so forth. The resulting thermochromic microcapsules typically have a size of from about 1 to about 50 micrometers, and in some embodiments, from about 3 to about 15 micrometers, Various other microencapsulation techniques may also be described in U.S. Pat. No. 4,957,949 to Kamada, et al. and U.S. Pat. No. 5,431,697 to Kamata, et al., which are incorporated herein in their entirety by reference thereto for all purposes. Suitable microencapsulated thermochromic substances may also be obtained from Matsui Shikiso Chemical Co., Ltd. of Kyoto, Japan under the designation "Chromicolor."

Thermochromic agents are commercially available from various sources. In one embodiment, for instance, thermochromic agents marketed by Chromatic Technologies, Inc. of Ithaca, N.Y. may be incorporated into the cleansing composition.

The thermochromic agents can be present in the cleansing composition in an amount sufficient to have a visual effect on the color of the composition. The amount or concentration of the agents can also be increased of decreased depending upon the desired intensity of any color.

As described above, thermochromic agents typically change from a specific color to clear at a certain temperature. If desired, other pigments or dyes can be added to the cleansing composition in order to provide a background color that remains constant independent of the temperature of the composition. By adding other pigments or dyes in combination with the thermochromic agents to the cleansing composition, the thermochromic agents can provide a color change at certain temperatures rather than just a loss of color should the thermochromic agent become clear. For instance, a non-thermochromic pigment, such as a yellow pigment, may be used in conjunction with a plurality of thermochromic agents, such as a red dye and a blue dye. When all combined together, the cleansing composition may have a dark color. As the composition is increased in temperature, the red thermochromic dye may turn clear changing the color to a green shade (a combination of yellow and blue). As the temperature further increases, the blue thermochromic dye turns clear causing the cleansing composition to turn yellow indicating to a user that a sufficient amount of washing has occurred.

Suitable non-thermochromic coloring agents which may be added to the cleansing composition include, for example, dyes, color additives, and pigments or lakes. Suitable dyes include, for example, Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin. Also, many dyes found suitable for use in the European Union and in Japan may be suitable for use as coloring agents in the present disclosure.

Suitable color additives include, for example, aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, manganese violet, mica, pyrophylite, silver, titanium dioxide, ultramarines, zinc oxide, and combinations thereof.

Suitable pigments or lakes include, for example, Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, Yellow 10 Lake, and combinations thereof.

It should be understood, that all different sorts of thermochromic agents and non-thermochromic pigments and dyes may be combined in order to produce a cleansing composition having a desired base color and one that undergoes desired color changes. The color changes, for instance, can be somewhat dramatic and fanciful. For instance, in one embodiment, the cleansing composition may change from green to yellow to red, such as the colors of a stop light, during a washing operation. Once the color of the composition turns red, a user would understand that sufficient time has elapsed and that the washing process is complete.

In an alternative embodiment, however, the composition can contain different thermochromic agents all having the same color. As the temperature of the composition is increased, however, the shade or intensity of the color can change. For instance, the composition can change from a vibrant blue to a light blue to a clear color during normal washing.

In addition to the above, it should be understood that many alterations and permutations are possible. Any of a variety of colors and shades can be mixed in order to undergo color changes as a function of temperature.

When thermochromic agents are used in conjunction with non-thermochromic pigments or dyes, the non-thermochromic pigments or dyes may comprise any suitable pigments or dyes that do not interfere with the cleansing composition or with the function of the thermochromic agents.

In one embodiment, in order to maintain the thermochromic agents dispersed throughout the cleansing composition, the thermochromic agents may be added to the cleansing composition in the presence of a suspending agent. The suspending agent can ensure that the thermochromic agents do not agglomerate or otherwise settle out of solution. In one embodiment, for instance, the suspending agent can ensure that the thermochromic agents do not agglomerate or otherwise settle out of solution. In one embodiment, for instance, the suspending agent may comprise an acrylic polymer such as an acrylate, that is designed to suspend the dyes and to stabilize and/or thicken the cleansing composition. For instance, in one embodiment, the suspending agent may comprise CARBOPOL AQUA SF-1 polymer available from Noveon, Inc. of Cleveland, Ohio. CARBOPOL AQUA SF-1 polymer is a lightly cross-linked acrylic polymer dispersion that has carboxyl functionality in its protonated form.

In one embodiment, a plurality of thermochromic agents may be present in the cleansing composition that cause a color change to occur over a temperature range of at least about 3° C. such as at least about 4° C., such as at least about 5° C., such as at least about 6° C. during cleansing. For instance, the color change can occur over a temperature range of from about 3° C. to about 20° C., such as from about 5° C. to about 10° C. The color change can be gradual as the cleansing composition increases in temperature or the color change may occur in a stepwise manner. For example, the color change may occur at every 2° C. increase in temperature, such as at every 3° C. increase in temperature, or at every 4° C. increase in temperature. Further, the color change may comprise a change from a certain color to a clear color, from one color to another color, or from one shade of a color to a lighter or darker shade.

The particular thermochromic agents that are combined together and used in the cleansing composition can be selected based upon the particular application and the desired results. In one embodiment, for instance, a first thermochromic agent may be present in the cleansing composition that causes an initial color change to occur at a temperature slightly above room temperature. For instance, the first color change can occur at a temperature of from about 23° C. to about 30° C., such as from about 25° C. to about 28° C. A second thermochromic agent may be present that causes a color change to occur at a temperature greater than the temperature at which the first thermochromic agent changes color. For example, the second thermochromic agent may change color at a temperature of from about 27° C. to about 35° C., such as from about 29° C. to about 32° C.

If desired, a third thermochromic agent may also be present in the cleansing composition that changes color at a temperature greater than the first and second thermochromic agents. For instance, if present, the third thermochromic agent may change color at a temperature of from about 31° C. to about 37° C., such as from about 34° C. to about 36° C. It should be understood, however, that more thermochromic agents may be present if desired. For instance, the cleansing composition may contain a thermochromic agent that causes a color change to occur at every 1° C. to 4° C. increase in temperature.

It should be understood, that the above temperature ranges are for exemplary purposes only. For instance, the above temperature ranges may be well suited to formulating a hand soap composition. When formulating a cleansing composition used to clean adjacent surfaces or objects, however, the composition may not increase in temperature to the extent as described above. Such cleansing compositions may include, for instance, disinfectants, general purpose cleaners, window cleaners, vehicle cleaners, and other similar cleaning products. For these products, the thermochromic agents may be incorporated into the cleansing composition so that the cleansing composition initially changes color at a relatively low temperature when the composition is used to clean, for instance, countertops, windows, and other similar objects. In still other embodiments, it may be desirable to have the initial color change occur at relatively high temperatures. For instance, if a particular cleaning product is to be used with warm water at a particular temperature, it may be preferred to have the initial color change occur at a temperature higher than the temperature of the water that is to be mixed with the product. With these considerations in mind, cleansing compositions made in accordance with the present disclosure that are intended to clean adjacent surfaces or objects may initially undergo a color change at a temperature of from about 15° C. to about 45° C., such as from about 21° C. to about 40° C.

Depending on the specific amount of heating agent incorporated into the cleansing composition, the temperature increase during use of the product may be relatively small. For instance, the increase in temperature during use of the product may be less than about 8° C., such as less than about 5° C. Thus, the thermochromic agents incorporated into the product may be configured to cause a color change to occur at every 1° C. to about 2° C. increase in temperature.

When the cleansing composition is intended to be used to clean a portion of a person's body, the heating and thermochromic agents present in the composition may be selected so that a color change occurs for a certain length of time after washing is initiated. For instance, if the cleansing composition is a hand soap, heating and thermochromic agents may be present in the composition so as to cause the composition to change color for at least about 20 seconds. For example, depending on the heating agents used, one can predict how much the formulation will increase in temperature during use. Based upon the temperature increase over a desired length of time, one can then specifically formulate a plurality of thermochromic agents sufficient to cause the color change to occur over the desired period of time.

As will be described in greater detail below, the heating and thermochromic agents can be incorporated into any suitable cleansing composition in accordance with the present disclosure. The cleansing composition, for instance, may be in a liquid form or in a solid form. When in a liquid form, the cleansing composition may have a relatively high viscosity or relatively low viscosity. The mixture of heating and thermochromic agents can also be incorporated into a cleansing composition that is intended to be aerated and form a foam such as a foam mousse as it is dispensed. As described above, each of these products may increase in temperature at a different rate during a typical washing exercise. The mixture of the thermochromic agents can be incorporated into the particular product and designed to provide a suitable indication when a sufficient period of time has passed to indicate that the desired temperature has been reached and washing, scrubbing, or wiping is complete.

As stated above, the plurality of heating and thermochromic agents may be combined with any suitable cleansing composition in accordance with the present disclosure. The cleansing composition can contain numerous different ingredients depending upon various factors, including the desired use of the product.

For many applications, the cleansing composition can contain one or more surfactants and/or one or more emollients, especially when the cleansing composition is used to clean part of a person's body, although surfactants are also used in numerous cleansing compositions designed to clean adjacent surfaces or objects. The surfactants and/or emollients can be contained in a carrier, such as water or an alcohol. In addition, the cleansing composition can contain sequestrants, non-aqueous solvents, preservatives, pH modifiers, disinfectants and various other optional ingredients. For exemplary purposes only, the following is a list of possible components that can be contained in the cleansing composition.

Surfactants

As described above, the cleansing composition can contain one or more surfactants. A surfactant can also serve as an emollient.

Nonionic, anionic, cationic, and amphoteric surfactants, such as zwitterionic surfactants, may all be suitable for use in the present disclosure. Nonionic surfactants typically have a hydrophobic base; such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty $C_8$-$C_{18}$) acids, condensation products of ethylene oxide with long chain amines or amides, condensation products of ethylene oxide with alcohols, and mixtures thereof.

Various specific examples of suitable nonionic surfactants include, but are not limited to, methyl gluceth-10, PEG-2-methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 cetyl ether, polyoxyethylene 10-oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, PEG 80 sorbitan laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Additional nonionic surfactants that can be used include water soluble alcohol ethylene oxide condensates, such as the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol® from Union Carbide Corp., Danbury, Conn. Specific examples of such commercially available nonionic surfactants of the foregoing type are $C_{11}$-$C_{15}$ secondary alkanols condensed with either 9 moles of ethylene oxide (Tergitol® 15-S-9) or 12 moles of ethylene oxide (Tergitol® 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal® CO-630 (a nonyl phenol ethoxylate) marketed by ISP Corp. (Wayne, N.J.). Suitable non-ionic ethoxylated octyl and nonyl phenols include those having from about 7 to about 13 ethoxy units. Such compounds are commercially available under the trade name Triton® X (Union Carbide, Danbury, Conn.).

Alkyl polyglycosides may also be used as a nonionic surfactant in the present inventive compositions. Suitable alkyl polyglycosides are known nonionic surfactants that are alkaline and electrolyte stable. Alkyl mono and polyglycosides are prepared generally by reacting a monosaccharide, or a compound hydrolyzable to a monosaccharide with an alcohol such as a fatty alcohol in an acid medium.

One example of such alkyl polyglycosides is APG™ 325 CS GLYCOSIDE, which is described as being a 50% $C_9$-$C_{11}$ alkyl polyglycoside, also commonly referred to as D-glucopyranoside. Another example of an alkyl polyglycoside surfactant is GLUCOPON™ 625 CS, which is described as being a 50% $C_{10}$-$C_{16}$ alkyl polyglycoside, also commonly referred to as a D-glucopyranoside. Both APG™ 325 CS GLYCOSIDE and GLUCOPON™ 625 CS are commercially available from Henkel Corp., Ambler, Pa. A particular surfactant that may be used is PLANTAREN 2000™, which is decyl glucoside.

Other useful nonionic surfactants include compositions based on amine oxides. One general class of useful amine oxides include alkyl di(lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl, dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide.

Another class of useful amine oxides include alkyl di(hydroxy lower alkyl) amine oxides in which the alkyl group has about 10-20, and particularly 12-16 carbon atoms, and can be straight or branched chain, saturated or unsaturated. Examples are bis(2-hydroxyethyl)cocoamine oxide, bis(2-hydroxyethyl)tallow amine oxide, and bis(2-hydroxyethyl) stearylamine oxide. Moreover, still other useful amine oxides include those characterized as alkylamidopropyl di(lower alkyl)amine oxides, in which the alkyl group has about 10-20 carbon atoms, and can be straight or branched chain, saturated or unsaturated. Examples are cocoamidopropyl dimethyl amine oxide and tallowamidopropyl dimethyl amine oxide.

Additional useful amine oxides include alkylmorpholine oxides in which the alkyl group has about 10-20 carbon atoms, and can be straight or branched chain, saturated or unsaturated. Further examples of amine oxides include those that commercially under the trade name AMMONYX (Stepan Co., Chicago, Ill.).

In addition to nonionic surfactants, the cleansing composition may also contain other types of surfactants. For instance, in some embodiments, amphoteric surfactants, such as zwitterionic surfactants, may also be used. For instance, one class of amphoteric surfactants that may be used in the present disclosure are derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

Additional classes of suitable amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, cocamidopropyl betaine, lauric myristic amido propyl monosodium phosphitaine, and mixtures thereof.

In certain instances, it may also be desired to utilize one or more anionic surfactants within the cleansing composition. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group can be straight chain (e.g., lauryl) or branched (e.g., 2-ethylhexyl). The cation of the anionic surfactant can be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Cationic surfactants, such as cetylpyridinium chloride and methylbenzethonium chloride, may also be utilized.

The amount of surfactant contained in the cleansing composition can vary greatly depending upon various factors. In some embodiments, the cleansing composition can contain surfactants in an amount from about 1% to about 60% by weight, such as from about 5% to about 40% by weight.

Emollients

The cleansing composition can also contain various emollients. In fact, some of the above described surfactants may be considered emollients. In one embodiment the emollient may comprise GLUCAM E-20™, methyl gluceth-20 available from Amerchol. Other emollients that may be particularly used include ethoxylated and propoxylated alcohols, such as cetyl alcohols and ethoxylated lanolin.

Non-Aqueous Solvents

In some instances, the cleansing composition may also include one or more non-aqueous solvents. Although not required, non-aqueous solvents can sometimes aid in dissolving certain components (e.g., preservatives, anti-microbial agent, etc.). Also, certain components in the cleansing composition may act as both an antimicrobial and a solvent. For example, an alcohol, such as ethanol, n-propanol, or isopropanol, may serve as both the antimicrobial and the non-aqueous solvent in a composition. Further examples of some suitable non-aqueous solvents include, but are not limited to, glycerine; glycols, such as propylene glycol, butylene glycol, triethylene glycol, hexylene glycol, polyethylene glycols, ethoxydiglycol, and dipropyleneglycol; triglycerides; ethyl acetate; acetone; triacetin; and combinations thereof. Solvent combinations include a glycol, particularly hexylene and/or propylene glycol, and one or more lower alcohols, particularly isopropanol, n-propanol, and/or ethanol.

Preservatives

The cleansing composition can also contain various preservatives to increase the shelf life of the composition.

Some suitable preservatives that can be used in the present disclosure include, but are not limited to, Kathon CG®, which is a mixture of methylchloroisothiazolinone and methylisothiazolinone available from Rohm & Haas; Mackstat H 66 (available from Mcintyre Group, Chicago, Ill.); DMDM hydantoin (e.g., Glydant Plus, Lonza, Inc., Fair Lawn, N.J.); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; imidazolidinyl urea; diazolidinyl urea; and the like. Other suitable preservatives include those sold by Sutton Labs, such as "Germall 115" (imidazolidinyl urea), "Germall II" (diazolidinyl urea), and "Germall Plus" (diazolidinyl urea and iodopropynyl butylcarbonate).

When utilized, the amount of the preservative utilized in the cleansing composition can generally vary depending on the relative amounts of the other components present within the formulation. For example, in some embodiments, the preservative is present in the formulation in an amount between about 0.001% to about 5% by weight, in some embodiments between about 0.001 to about 1% by weight, and in some embodiments, between about 0.1% to about 0.15% by weight of the disinfectant formulation.

pH Modifiers

In general, the pH of the cleansing composition may be controlled to be within any desired range.

If necessary, various pH modifiers may be utilized in the cleansing composition to achieve the desired pH level. For instance, some examples of basic pH modifiers that may be used in the present disclosure include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; tetrahydroxypropyl ethylene-diamine; and triethanolamine.

Moreover, some examples of acidic pH modifiers that may be used in the present disclosure include, but are not limited to, mineral acids; and carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly (methacrylic) acid, and naturally occurring polymeric acids such as carageenic acid, and alginic acid.

Sequestrants

In one embodiment, the cleansing composition may contain one or more sequestrants. A sequestrant is a substance whose molecules can form one or more bonds with a metal ion. In particular, water often contains metal ions, such as calcium ions, that might react with anionic components (e.g., surfactants, acids, etc.) present within the composition. For example, in one embodiment, a surfactant that remains substantially unreacted with metal ions can better function as a cleansing agent.

Some examples of sequestrants that may be used in the cleansing composition of the present disclosure include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and the like.

Carrier

For many applications, the cleansing composition may contain a carrier for the various components. For instance, an alcohol and/or water may be used as a carrier. If an alcohol is used as the carrier in the cleansing composition, then the alcohol may or may not be simultaneously acting as the antimicrobial and/or solvent.

Water, when used, can be included in an amount sufficient to control the viscosity of the composition. In this regard, water can be present in an amount from about 1% to about 99% by weight, such as from about 40% to about 99% by weight.

For example, the amount of water added to the composition can be controlled so as to produce a cleansing composition that has a relatively high viscosity or relatively low viscosity. Cleansing compositions that are intended to foam when dispensed, for instance, typically have a relatively low viscosity.

Heat Sink Particles

Additionally, the cleansing composition may comprise heat sink particles, designed specifically to maintain the increased temperature of the cleansing composition. Once the cleansing composition has reached a maximum temperature, the heat sink particles will retain heat, allowing the cleansing composition to remain heated for an extended time. Suitable materials to act as heat sink particles include clay, clay-like materials, quartz particles, silica, silicates, and combinations thereof. The amount of heat sink particles present within the cleansing composition can vary depending upon various factors and the desired results. In general, for instance, the heat sink particles can be present in an amount from about 0.01% to about 25% by weight, such as from about 0.5% to about 5% by weight.

Other Optional Ingredients

In order to better enhance the composition, other optional ingredients can also be used. For instance, some classes of ingredients that can be used include, but are not limited to: antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); deodorants (reduce or eliminate unpleasant odor and protect against the formation of malodor on body surfaces); external analgesics (a topically applied drug that has a topical analgesic, anesthetic, or antipuretic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some anti-microbial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); sunscreens and thickeners (such as acrylate copolymers, to increase the viscosity of the formulation).

In an alternative embodiment of the present disclosure, the heating and thermochromic agents in the cleansing composition can be combined with one or more other active ingredients to impart additional benefits to the end user; that is, the cleansing composition may comprise two or more active agents. The two or more active agents may include a heating agent, or may not include a heating agent. Also, the cleansing composition may include a single active agent that is not a heating agent. Additionally, the active agent or combination of active agents can be located in one or more of the layers surrounding the heating or thermochromic agents, for example, in the encapsulation layer. Also, the active agent or combination of active agents can be located in-between two of the layers on the encapsulated heating or thermochromic agents.

A number of alternative or additional active agents are suitable for inclusion in the cleansing composition. Active agents such as neurosensory agents (agents that induce a perception of temperature change without involving an actual change in temperature such as, for example peppermint oil, eucalyptol, eucalyptus oil, methyl salicylate, camphor, tea tree oil, ketals, carboxamides, cyclohexanol derivatives, cyclohexyl derivatives, and combinations thereof), cleansing agents (e.g., enzymes), appearance modifying agents (e.g., exfoliation agents, skin-firming agents, anti-callous agents, anti-acne agents, anti-aging agents, anti-wrinkle agents, anti-dandruff agents, antiperspirant agents, wound care agents, enzyme agents, scar repair agents, colorant agents, humectant agents, hair care agents such as conditioners, styling agents, and detangling agents), powders, skin coloration agents such as tanning agents, lightening agents, and brightening agents, shine control agents and drugs), nutrients (e.g., anti-oxidants, transdermal drug delivery agents, botanical extracts, vitamins, magnets, magnetic metals, foods, and drugs), pesticides (e.g., anti-bacterials, anti-virals, anti-fungals, preservatives, insect repellants, anti-acne agents, anti-dandruff agents, anti-parasite agents, wound care agents, and drugs), surface conditioning agents (e.g., pH adjusting agents, moisturizers, skin conditioners, exfoliation agents, shaving lubricants, skin-firming agents, anti-callous agents, anti-acne agents, anti-aging agents, anti-wrinkle agents, anti-dandruff agents, wound care agents, skin lipids, enzymes, scar care agents, humectants, powders, botanical extracts, and drugs), hair care agents (e.g., shaving lubricants, hair growth inhibitors, hair growth promoters, hair removers, anti-dandruff agents, colorant agents, humectants, hair care agents such as conditioners, styling agents, detangling agents, and drugs), anti-inflammatory agents (e.g., skin conditioners, external analgesic agents, anti-irritant agents, anti-allergy agents, anti-inflammatory agents, wound care agents, transdermal drug delivery, and drugs), emotional benefit agents (e.g., gas generating agents, fragrances, odor neutralizing materials, exfoliation agents, skin-firming agents, anti-callous agents, anti-acne agents, anti-aging agents, soothing agents, calming agents, external analgesic agents, anti-wrinkle agents, anti-dandruff agents, antiperspirants, deodorants, wound care agents, scar care agents, coloring agents, powders, botanical extracts and drugs), indicators (e.g., soil indicators), and organisms.

Additional suitable active agents include abrasive materials, abrasive slurries, acids, adhesives, aldehydes, animal feed additives, antioxidants, appetite suppressants, bases, biocides, blowing agents, botanical extracts, candy, carbohydrates, carbon black, carbonless copying materials, catalysts, ceramic slurries, chalcogenides, colorants, cooling agents, corrosion inhibitors, curing agents, detergents, dispersants, EDTA, enzymes, exfoliation, fats, fertilizers, fibers, fire retardant materials, flavors, foams, food additives, fragrances, fuels, fumigants, gas forming compounds, gelatin, graphite, growth regulators, gums, herbicides, herbs, spices, hormonal based compounds, humectants, hydrides, hydrogels, imaging materials, ingredients that are easily oxidized or not UV stable, inks, inorganic oxides, inorganic salts, insecticides, ion exchange resins, latexes, leavening agents, liquid crystals, lotions, lubricants, maltodextrins, medicines, metals, mineral supplements, monomers, nanoparticles, nematicides, nicotine-based compounds, oil recovery agents, organic solvents, paint, peptides, pesticides, pet food additives, phase change materials, phase change oils, pheromones, phosphates, pigments, dyes, plasticizers, polymers, propellants, proteins, recording materials, silicates, silicone oils, stabilizers, starches, steroids, sugars, surfactants, suspensions, dispersions, emulsions, vitamins, waste treatment materials, adsorbents, water insoluble salts, water soluble salts, water treatment materials, and waxes.

As described above, the cleansing composition of the present disclosure may be produced in liquid form or in a solid form, which can impact the type of ingredients that are present in the composition. In one embodiment, the antimicrobial, heating, and thermochromic agents can be incorporated into a solid cleansing composition intended to be used to clean the hands, the face, and/or the body of a user. In one embodiment, the antimicrobial, heating, and thermochromic agents may be incorporated into an alkali soap in the form of a soap bar. Alkali soaps are well known in the art. Such soaps are typically formed from an acid-base composition. The soaps, for instance, can contain an acid, such as a fatty acid that is neutralized with a base. The acid may comprise, for instance, tallow which comprises primarily triglycerides of stearic, palmitic, and oleic acids. The tallow can be combined with, for instance, lye in order to form the soap.

The antimicrobial, heating, and thermochromic agents can also be incorporated into solid cleansers made from synthetic materials. Such cleansers can be made from, for instance, a flaked surfactant such as sodium cocoyl isethionate. These cleansers can also contain various fillers, such as dextrin.

In still another embodiment, the antimicrobial, heating, and thermochromic agents may be incorporated into a solid glycerine soap. Glycerine soap typically contains glycerine combined with conventional soap materials, such as tallow and lye in addition to an alcohol, such as a fatty alcohol, and a sugar. Glycerine soaps can be translucent when formed.

It should be understood, that the solid cleansing compositions as described above including solid soaps, solid cleansers, and glycerine soaps, can contain various other additives as desired. For instance, various oils, moisturizers, fragrances, dyes, preservatives, and other cosmetic ingredients may be contained within the product.

In addition to the liquid and solid forms of the cleansing composition as previously presented, the cleansing composition of the present disclosure is suitable for use in a number of products, including wipe products, personal care products, cleansers, lotions, emulsions, oils, ointments, salves, balms, and the like. The following description relates primarily to the cleansing composition as incorporated into a wiping product; however, it will be recognized by one skilled in the art that the cleansing composition described herein could be incorporated into any one or more of the other products listed above.

Referring now to the drawings, FIG. 1 shows a perspective view of a dispenser for disposable wipes 10 in accordance with the present disclosure. The dispenser 10 comprises a dispensing container 12. The dispensing container 12 is generally in the shape of a cylinder having a side wall 14, a dispensing wall 15, and a bottom wall (not shown). Dispensing wall 15 is adjacent to the side wall 14 of the dispensing container 12. Dispensing wall 15 has a central aperture 16 located generally in the center of the dispensing wall 15. A lead wipe 18 is shown at the top of the dispensing container 12. This single wipe is shown as being removed from the dispensing container 12 through the central aperture 16.

FIG. 1 shows one embodiment of the present disclosure, in which the cleansing composition is incorporated into a wiping product. Generally, the wipes of the present disclosure including the cleansing composition can be wet wipes or dry wipes. As used herein, the term "wet wipe" means a wipe that includes greater than about 70% (by weight substrate) moisture content. As used herein, the term "dry wipe" means a wipe that includes less than about 10% (by weight substrate) moisture content. Specifically, suitable wipes for use in the present disclosure can include wet wipes, hand wipes, face wipes, cosmetic wipes, household wipes, industrial wipes, and the like. Particularly preferred wipes are wet wipes, and other wipe-types that include a solution.

Materials suitable for the substrate of the wipes are well know to those skilled in the art, and are typically made from a nonwoven fibrous sheet material. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, the wipes of the present disclosure define a basis weight of from about 25 grams per square meter to about 120 grams per square meter and desirably from about 40 grams per square meter to about 90 grams per square meter.

In one particular embodiment, the wipes of the present disclosure comprise a coform basesheet of polymer fibers and absorbent fibers having a basis weight of from about 60 to about 80 grams per square meter and desirably about 75 grams per square meter. Such coform basesheets are manufactured generally as described in U.S. Pat. No. 4,100,324, issued to Anderson, et al. (Jul. 11, 1978); U.S. Pat. No. 5,284, 703, issued to Everhart, et al. (Feb. 8, 1994); and U.S. Pat. No.

5,350,624, issued to Georger, et al. (Sep. 27, 1994), which are incorporated by reference to the extent to which they are consistent herewith. Typically, such coform basesheets comprise a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated PLTD-1810, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials or combinations thereof may alternatively be utilized as known in the art.

As noted above, the coform basesheet additionally may comprise various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Washington); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may comprise from about 10 weight percent to about 90 weight percent, desirably from about 20 weight percent to about 60 weight percent, and more desirably from about 25 weight percent to about 35 weight percent of the polymeric meltblown fibers based on the dry weight of the coform basesheet being used to provide the wipes.

When the fibrous sheet material is a coform basesheet comprising a matrix of thermoplastic polymeric meltblown fibers and absorbent cellulosic fibers, a stream of cleansing composition can be merged with a stream of cellulosic fibers and a stream of polymeric fibers into a single stream and collected on a forming surface such as a forming belt or forming drum to form a wipe comprising a fibrous sheet material with the cleansing composition within its core.

In accordance with the present disclosure, the contents (i.e., heating and thermochromic agents) of the cleansing composition as described herein are capable of generating heat to produce a warming sensation and a color change in the wipe upon use. When the heating agent is activated, an exothermic reaction occurs, which causes the thermochromic agent to become activated, thereby warming and changing the color of the wipe. In one embodiment, the wipe is a wet wipe comprising a wetting solution in addition to the fibrous sheet material and the cleansing composition. The wetting solution of the previous embodiment can be any wetting solution known to one skilled in the wet wipe art. Generally, the wetting solution can include water, emollients, surfactants, preservatives, chelating agents (such as disodium EDTA), pH adjusting agents, skin conditioners, fragrances, and combinations thereof. For example, one suitable wetting solution for use in the wet wipe of the present disclosure comprises about 98% (by weight) water, about 0.6% (by weight) surfactant, about 0.3% (by weight) humectant, about 0.3% (by weight) emulsifier, about 0.2% (by weight) chelating agent, about 0.35% (by weight) preservative, about 0.002% (by weight) skin conditioning agent, about 0.03% (by weight) fragrance, and about 0.07% (by weight) pH adjusting agent. One specific wetting solution suitable for use in the wet wipe of the present disclosure is described in U.S. Pat. No. 6,673,358, issued to Cole et al. (Jan. 6, 2004), which is incorporated herein by reference to the extent it is consistent herewith.

In another embodiment, the wipe is a dry wipe wherein the cleansing composition comprising an antimicrobial agent, a heating agent, and a thermochromic agent is added to the wipe in dry form. Upon contacting water or any other suitable solvent, the cleansing composition of the present disclosure is activated. In this embodiment, the wipe can be wetted with an aqueous solution just prior to, or at the point of, use of the wipe. The aqueous solution can be any aqueous solution known in the art to be suitable for use in wipe products. Generally, the aqueous solution includes mainly water, and can further include additional components, such as cleansers, lotions, preservatives, fragrances, surfactants, emulsifiers, and combinations thereof. Once the wipe is wetted with the aqueous solution and the contents of the cleansing composition contact the aqueous solution, an exothermic reaction similar to the wet wipe embodiment above is produced, thereby warming and changing the color of the wipe.

A conventional wipe will typically be stored at room temperature (about 23° C. (73.4° F.). As such, when the heating agent is activated, a warming sensation is produced, increasing the temperature of the solution and wipe by at least about 5° C. More suitably, the temperature of the solution and wipe is increased by at least about 10° C., even more suitably, increased by at least about 15° C., and even more suitably increased by at least about 20° C. or more.

Generally, the elapsed time between the dispensing of a wipe product and use of the product is about 2 seconds or less, and typically is about 6 seconds or less. As such, upon activation the heating agent of the cleansing composition begins to generate heat and a warming sensation is suitably perceived in less than about 20 seconds. More suitably, the warming sensation is perceived in less than about 10 seconds, even more suitably, in less than about 5 seconds, and even more suitably, in less than about 2 seconds.

Additionally, once the warming sensation begins, the warming sensation of the wipe product is suitably maintained for at least about 5 seconds. More suitably, the warming sensation is maintained for at least about 8 seconds, even more suitably for at least about 15 seconds, even more suitably for at least about 20 seconds, even more suitably for at least about 40 seconds, and even more suitably for at least about 1 minute.

The color change which results from the warming of the wipe may occur gradually, as the wipe increases in temperature. For example, as the wipe is used it may gradually go from a dark color to a lighter color. While the temperature and color may change simultaneously, in another embodiment the thermochromic agent may activate only once a specific temperature is reached. Therefore, the only color change during the cleansing process may occur at the point at which the cleansing composition reaches the desired temperature.

To generate the temperature increase described above, the wipes of the present disclosure suitably comprise from about 0.33 grams per square meter to about 500 grams per square meter cleansing composition. More suitably, the wipes comprise from about 6.0 grams per square meter to about 175 grams per square meter cleansing composition, even more suitably from about 16 grams per square meter to about 90 grams per square meter, and even more suitably, from about 30 grams per square meter to about 75 grams per square meter cleansing composition.

The cleansing composition can be applied to the wipe using any means known to one skilled in the art. For instance, the cleansing composition can be embedded into the core of the fibrous sheet material of the wipe. By embedding the cleansing composition into the core of the fibrous sheet material, the wipe will have a reduced grittiness feel because of a cushion effect. Additionally, when the cleansing composition is located in the core of the fibrous sheet material, the cleansing composition is better protected from premature activation caused by the conditions of manufacturing, storage, and transportation of the wipe.

The thickness of the fibrous sheet material will depend upon the fibrous sheet material basis weight and the cleansing composition loading. Also, in the embodiments in which either one or both of the heating and thermochromic agents are encapsulated, the diameter size of the encapsulated agents will affect the thickness of the fibrous sheet material. For example, as the size of the encapsulated heating and/or thermochromic agents is increased, the fibrous sheet material can be thicker to prevent the wipe from having a gritty feel.

In another embodiment, the fibrous sheet material is made up of more than one layer. For example, when the fibrous sheet material is a meltblown material, the fibrous sheet material can suitably be made up of two meltblown layers secured together, more suitably three meltblown layers, even more suitably four meltblown layers, and even more suitably five or more meltblown layers. When the fibrous sheet material is a coform basesheet, the fibrous sheet material can suitably be made up of two coform basesheet layers secured together, more suitably three coform basesheet layers, even more suitably four coform basesheet layers, even more suitably five or more coform basesheet layers. Moreover, when the fibrous sheet material includes a film, the fibrous sheet material can suitably be made up of two film layers, more suitably three film layers, even more suitably four film layers, and even more suitably five or more film layers. In one embodiment, the layers are separate layers. In another embodiment, the layers are plied together.

Figure 2:
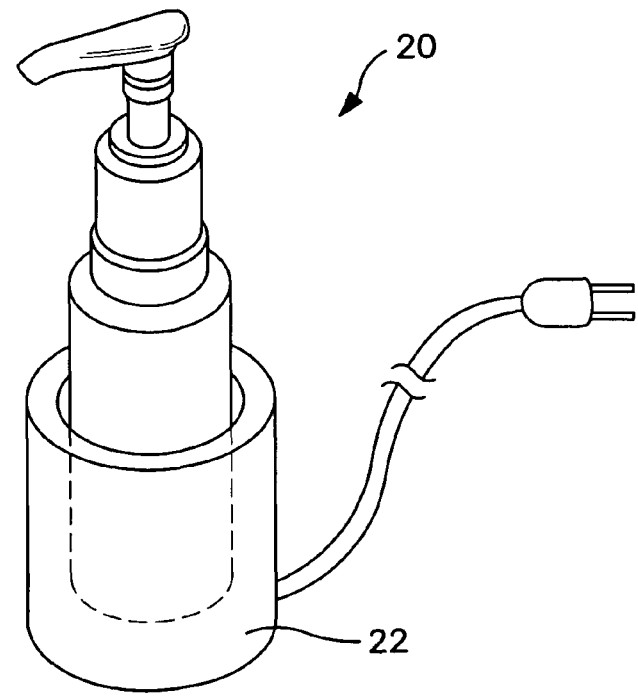
FIG. 2 is a perspective view of one embodiment of a liquid cleansing composition heated by an external heating source.
Figure 3:
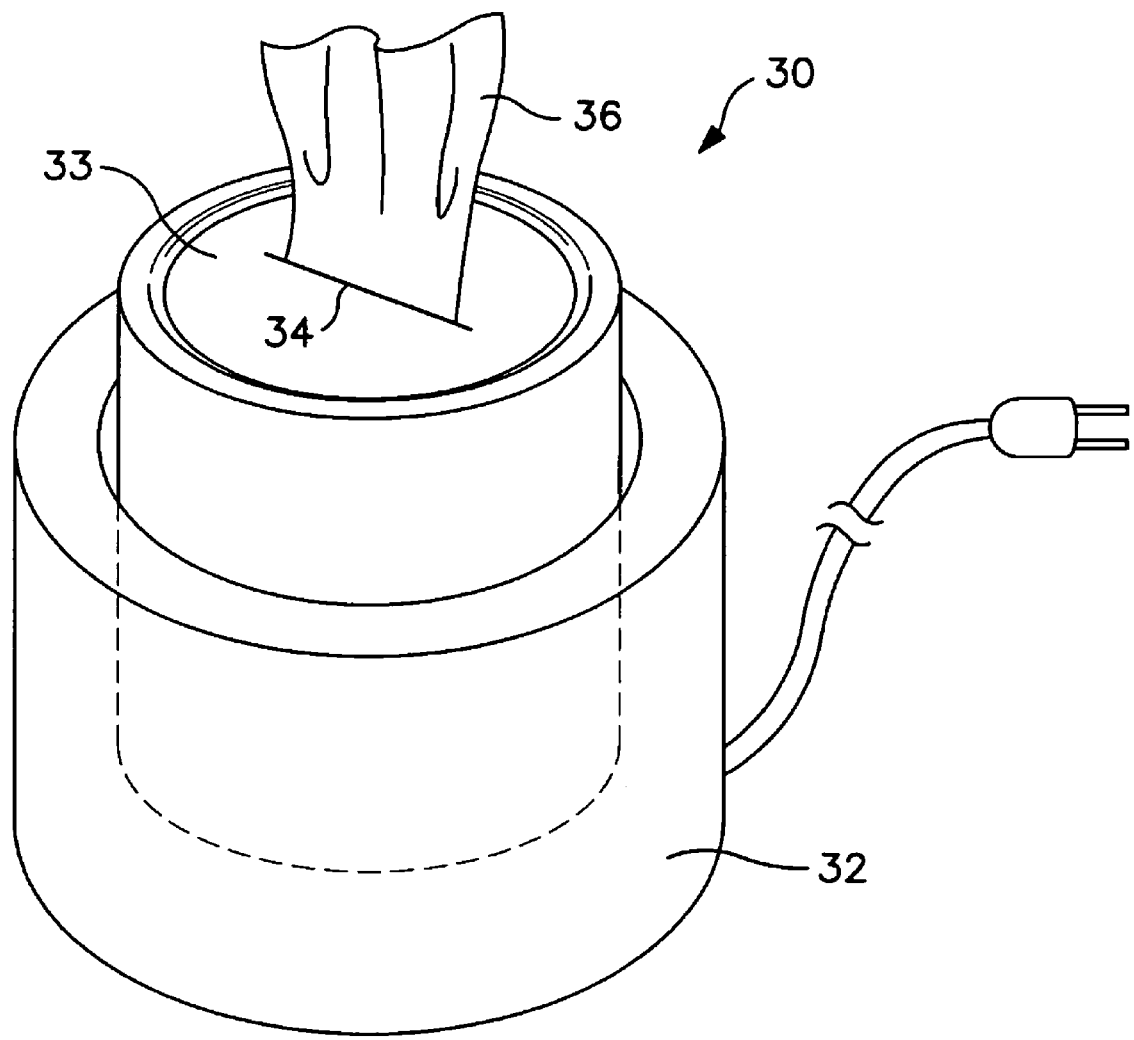
FIG. 3 is a perspective view of one embodiment of a cleansing composition as contained in a wiper product, the wiper product heated by an external heating source.

Referring again to the drawings, FIG. 2 and FIG. 3 show two additional embodiments of the present disclosure, in which the cleansing composition is heated by a heating source rather than the cleansing composition comprising a heating agent.

FIG. 2 shows a cleansing composition dispenser 20, and particularly a hand soap dispenser. The dispenser 20 contains the cleansing composition of the present disclosure. A heating source 22, specifically an electrical resistance heater, heats the dispenser 20, thereby heating the cleansing composition contained in the dispenser, activating the thermochromic agent, and causing the cleansing composition to change color.

Another embodiment of the present disclosure is shown in FIG. 3. A wipe dispenser 30 is heated by a heating source 32, which is an electrical resistance heater. The heat transferred from the heating source 32 to the dispenser 30 is then transferred to a stack of wipes (not shown) inside the dispenser, the wipes comprising the cleansing composition of the present disclosure. Upon heating, the thermochromic agent present in the cleansing composition activates and the wipes change color. A central aperture 34 is present in the middle of the dispensing wall 33. When wipes have reached the desired temperature, lead wipe 36 may be pulled from the stack of wipes inside wipe dispenser 30.

As discussed above in alternative embodiments of the present disclosure, the cleansing system may comprise a heating source rather than a heating agent. Both the heating source and the heating agent serve to increase the temperature of the cleansing composition; however, the heating source heats the cleansing composition from the outside while the heating agent heats from within the composition.

The heat source of the present disclosure may be used to heat a liquid cleansing composition, a solid cleansing composition, a wipe comprising a cleansing composition, or any other suitable form. The heat source increases the temperature of the cleansing composition, which activates the thermochromic agent present in the cleansing composition and signals to the user that the cleansing composition is at a desirable temperature for microbe removal. Although the heating agent and the heating source produce the same results, the temperature increase is achieved through different means.

The embodiments shown in FIG. 2 and FIG. 3 comprise electrical resistance heaters. However, the heating source of the present disclosure may comprise a microwave heater, an infrared heater, or any other suitable heat source.

EXAMPLES

The following are examples of cleansing compositions, such as a hand sanitizer or a surface sanitizer, that may be made in accordance with the present disclosure.

Example 1

TABLE 1

Warming Color Indicator Hand Sanitizer
Batch Size (in grams) 800.00

| Trade Name | Ingredient | % wt | Grams | Range in Formulation | Supplier |
|---|---|---|---|---|---|
| Phase A | | | | | |
| Water | | 25.65 | 205.20 | 0.1-40% | |
| VERSENE NA2 | disodium EDTA | 0.10 | 0.80 | Additive | |
| CARBOPOL ETD 2020 | acrylate copolymer | 0.50 | 4.00 | 0.1-10% | Noveon |
| Phase B | | | | | |
| GLUCAM E-20 | methyl gluceth-20 | 2.00 | 16.00 | Additive | Amerchol |
| SD Alcohol 40B | ethanol | 60.00 | 480.00 | 60-80% | |

TABLE 1-continued

Warming Color Indicator Hand Sanitizer
Batch Size (in grams) 800.00

| Trade Name | Ingredient | % wt | Grams | Range in Formulation | Supplier |
|---|---|---|---|---|---|
| Phase C | | | | | |
| NEUTROL TE | tetrahydroxypropyl ethylene-diamine | 0.55 | 4.40 | Additive | |
| Phase D | | | | | |
| Fragrance | | 0.20 | 1.60 | Additive | |
| CCC 25C Thermochromatic Slurry | thermochromic dye | 1.00 | 8.00 | 0.1-3% | |
| Wax Coated Magnesium Chloride | | 10.00 | 80.00 | 5-30% | Aveka |
| Total | | 100.00 | 800.00 | | |

As shown above, the hand sanitizer contains only one thermochromic agent, CCC 25C Thermochromatic Slurry. The heating agent of the above composition is the wax coated magnesium chloride. The antimicrobial agent of the hand sanitizer composition shown is SD Alcohol 40B, which is ethanol.

In addition to the antimicrobial, heating, and thermochromic agents, the hand sanitizing composition contains other components. Phase A contains disodium EDTA (VERSENE NA2) which acts as a chelating agent in the composition. Another component of Phase A is CARBOPOL ETD 2020, an acrylate copolymer that acts as a thickener in the cleansing composition. The emollient present in the hand sanitizer composition is GLUCAM E-20 (methyl gluceth-20). Additionally, the hand sanitizer comprises a base neutralizer (NEUTROL TE) and a fragrance.

In order to combine the above ingredients into a hand cleansing composition, Phase A was first blended together with medium to high shear until the thickener was dispersed and homogeneous. The ingredients of Phase B were then added and the composition was mixed until it reached a homogeneous state. The pH of the solution was adjusted using the base neutralizer, NEUTROL TE. However, a neutralizer of choice could be used to adjust the pH to a range of 6.8 to 7.4. A fragrance was added, and the composition was mixed until homogeneous. Finally, the remainder of Phase D, the thermochromic and heating agents, were added.

Example 2

TABLE 2

Warming Color Indicator Surface Sanitizer Wipe or Spray Liquid
Batch Size (in grams) 800.00

| Trade Name | Ingredient | % wt | Grams | Range in Formulation | Supplier |
|---|---|---|---|---|---|
| Phase A | | | | | |
| Water | | 27.30 | 218.40 | 0.1-40% | |
| HEC | hydroxy ethyl cellulose | 1.00 | 8.00 | 0.01-10% | |
| Phase B | | | | | |
| SD Alcohol 40B | ethanol | 60.00 | 480.00 | 60-80% | |
| Phase C | | | | | |
| PLANTAREN 2000 | decyl glucoside | 0.50 | 4.00 | Additive | |
| Fragrance | | 0.20 | 1.60 | Additive | |
| CCC 25C Thermochromatic Slurry | thermochromic dye | 1.00 | 8.00 | 0.1-3% | |
| Wax Coated Magnesium Chloride | | 10.00 | 80.00 | 5-30% | Aveka |
| Total | | 100.00 | 800.00 | | |

As shown above, the surface sanitizer wipe or spray liquid comprises a single thermochromic agent, CCC 25C Thermochromatic Slurry. Phase B is the antimicrobial agent, SD Alcohol 40B, which is ethanol. The heating agent of the sanitizer composition is wax coated magnesium chloride.

Phase A of the surface sanitizer composition contains HEC (hydroxylethyl cellulose), a thickener. In addition to the above mentioned components, the composition contains a fragrance and the nonionic surfactant PLANTAREN 2000 (decyl glucoside).

In order to combine the above ingredients to create one embodiment of the present disclosure, Phase A was first mixed until homogeneous. Phase B was then added and mixed. Finally, the ingredients of Phase C were added in order and mixed until homogeneous.

Example 3

TABLE 3

Warming Anti-Bacterial Cleanser
Batch Size (in grams) 100.00

| Trade Name | INCI Name | % wt | Grams | Supplier |
|---|---|---|---|---|
| Phase 1 | | | | |
| AEROSIL 300 | Silica | 4.00 | 4.00 | Degussa |
| Denatured Ethyl Alcohol | SD Alcohol 40B | 65.00 | 65.00 | Grain Processing Corporation |
| ULTRASIL SW 12 | Dimethicone PEG-7 Cocoate | 3.00 | 3.00 | Noveon |
| MACKANATE CM 100 | Disodium Cocamido MEA-Sulfosuccinate | 8.00 | 8.00 | McIntyre Chemical |
| CROVOL PK-70 | PEG-45 Palm Kernel Glycerides | 3.50 | 3.50 | Croda |
| Benzalkonium Chloride | Benzalkonium Chloride | 0.50 | 0.50 | Sigma |
| CCC 25C Thermochromic Slurry | | 1.00 | 1.00 | |
| Magnesium Sulfate | Magnesium Sulfate | 15.00 | 15.00 | Sigma |
| Total | | 100.00 | 100.00 | |

The cleansing composition shown in the Table 3 comprises a single thermochromic agent, a heating agent, and two antimicrobial agents. The thermochromic and heating agents are CCC 25C Thermochromic Slurry and Magnesium Sulfate, respectively. The two antimicrobial agents used in the given cleansing composition are denatured ethyl alcohol and benzalkonium chloride.

In order to create a cleansing composition with the ingredients listed in Table 3, first the ethanol was weighed and AEROSIL 300 was added with moderate agitation until a gel formed. The composition was then mixed as the rest of the materials were added. The cleansing composition was mixed further until it reached a homogeneous state.

The cleansing composition of the present example was tested through an observational test. The cleansing composition was applied into the hands, which were rubbed lightly together. During the cleansing process a cold sensation was felt first, which presumably indicated that the alcohol was evaporating. After about 15-20 seconds the hands were placed under cold water and rubbed vigorously together. A dramatic warming sensation, copious foam formation, and a color change were observed during the cleansing process. After the color of the composition changed to the final color indicator, the hands were rinsed.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed:

1. A cleansing composition comprising:
an antimicrobial agent present in an amount of at least 50 percent by weight but not more than 70 percent by weight, wherein the antimicrobial agent selected from a group consisting of an alcohol, an isothiazolone, alkyl dimethyl ammonium chloride, a triazine, 2-thiocyanomethylthio benzothiazol, methylene bis thiocyanate, acrolein, dodecylguanidine hydrochloride, a chlorophenol, gluteraldehyde, a dithiocarbamate, 2-mercatobenzothiazole, para-chloro-meta-xylenol, silver, chlorohexidine, polyhexamthylene biguanide, a n-halamine, triclosan, a phospholipid, an alpha hydroxyl acid, 2,2-dibromo-3-nitrilopropionamide, 2-bromo-2-nitro-1,3-propanediol, farnesol, iodine, bromine, chlorine dioxide, ozone, a botanical oil, a botanical extract, chlorine, sodium hypochlorite, and combinations thereof, and at least 5 percent by weight of a heating agent in an aqueous carrier, the heating agent being configured to activate during use of the cleansing composition causing an increase in temperature of the composition, the cleansing composition further comprising a thermochromic agent, the thermochromic agent being configured to cause a change in color of the cleansing composition during the increase in temperature due to the activation of the heating agent; and
water in an amount greater than 5 percent by weight,
wherein the heating agent increases the temperature of the cleansing composition of from 20° C. to 25° C. when activated.

2. A cleansing composition as defined in claim 1, wherein the alcohol comprises ethanol.

3. A cleansing composition as defined in claim 1, wherein the heating agent is an electrolyte salt that undergoes an exothermic reaction when contacted with water.

4. A cleansing composition as defined in claim 3, wherein the electrolyte salt is encapsulated with a material that degrades during use of the cleansing composition.

5. A cleansing composition as defined in claim 1, wherein the heating agent is encapsulated with a material that degrades during use of the cleansing composition.

6. A cleansing composition as defined in claim 5, wherein the material used to encapsulated the heating agent comprises a wax.

7. A cleansing composition as defined in claim 1, wherein the heating agent comprises calcium chloride, magnesium chloride, a zeolite, aluminum chloride, calcium sulfate, magnesium sulfate, sodium carbonate, sodium sulfate, sodium acetate, a metal, slaked lime, quick lime, a glycol, polyvinyl amine, polyalkyleneamine, polyalkyleneimine, a metal oxide, an electrolyte salt or combinations thereof.

8. A cleansing composition as defined in claim 3, wherein the electrolyte salt is magnesium chloride.

9. A cleansing composition as defined in claim 1, wherein the thermochromic agent comprises a leuco dye.

10. A cleansing composition as defined in claim 1, wherein the cleansing composition is a liquid.

11. A cleansing composition as defined in claim 1, wherein the cleansing composition is a solid.

12. A cleansing composition as defined in claim 1, wherein the heating agent is present in the cleansing composition in an amount sufficient to cause the cleansing composition to increase in temperature from 20° C. to about 40° C. when activated.

13. A wiper product comprising a substrate containing the cleansing composition defined in claim 1.

14. A wiper product as defined in claim 13, wherein the substrate comprises a nonwoven fibrous sheet material selected from the group consisting of meltblown, coform, air-laid, bonded carded web materials, hydroentangled materials and combinations thereof.

15. A cleansing composition as defined in claim 1, wherein the cleansing composition comprises at least one surfactant.

16. A cleansing composition as defined in claim 1, wherein the thermochromic agent is configured to change color at a temperature of at least about 25° C.

17. A cleansing composition as defined in claim 1, wherein the thermochromic agent is configured to change color at a temperature of at least about 30° C.

18. A cleaning composition as defined by claim 1, wherein the heating agent is present in an amount of at least 5 percent but not more than 40 percent by weight.

19. A cleaning composition as defined by claim 1 wherein the heating agent is present in an amount of at least 5 percent but not more than 30 percent by weight.

20. A cleaning composition as defined by claim 1 wherein the heating agent is present in an amount of at least 10 percent but not more than 25 percent by weight.

21. A cleaning composition as defined by claim 1 wherein the cleaning composition includes heat sink particles.

22. A cleaning composition as defined by claim 1 wherein the temperature increase is at least 10 degrees Celsius.

23. A cleaning composition as defined by claim 1 wherein the temperature increase is at least 15 degrees Celsius.

24. A cleaning composition as defined by claim 1 wherein the temperature increase is at least 20 degrees Celsius.

* * * * *